(12) United States Patent
Seligman (10) Patent No.: US 11,766,349 B2
(45) Date of Patent: Sep. 26, 2023

(54) LOW PROFILE KNEE BRACE AND METHOD OF USING SAME

(71) Applicant: DJO, LLC, Vista, CA (US)

(72) Inventor: Scott Seligman, Vista, CA (US)

(73) Assignee: DJO, LLC, Carlsbad, CA (US)

( * ) Notice: Subject to any disclaimer, the term of this patent is extended or adjusted under 35 U.S.C. 154(b) by 560 days.

(21) Appl. No.: 14/831,709

(22) Filed: Aug. 20, 2015

(65) Prior Publication Data

US 2016/0051389 A1    Feb. 25, 2016

Related U.S. Application Data

(60) Provisional application No. 62/039,716, filed on Aug. 20, 2014.

(51) Int. Cl.
*A61F 5/00* (2006.01)
*A61F 5/01* (2006.01)

(52) U.S. Cl.
CPC .......... *A61F 5/0125* (2013.01); *A61F 5/0123* (2013.01); *A61F 2005/0137* (2013.01); *A61F 2005/0172* (2013.01)

(58) Field of Classification Search
CPC .................. A61F 5/0123; A61F 5/0125; A61F 2005/0137; A61F 2005/0144; A61F 2005/0172; A61F 2005/0174; A61F 2005/0176
USPC ............................................. 602/16, 23, 26
See application file for complete search history.

(56) References Cited

U.S. PATENT DOCUMENTS

| | | | | |
|---|---|---|---|---|
| 2,144,641 A | * | 1/1939 | Snyder | A61F 5/0125 2/22 |
| 3,350,719 A | * | 11/1967 | McClure, Jr. | A61F 5/0123 2/22 |
| 3,817,244 A | * | 6/1974 | Taylor | A61F 5/0123 602/26 |
| 4,312,335 A | * | 1/1982 | Daniell, Jr. | A61F 5/0125 602/16 |
| 4,628,916 A | * | 12/1986 | Lerman | A61F 5/0123 602/16 |

(Continued)

FOREIGN PATENT DOCUMENTS

| | | |
|---|---|---|
| EP | 1829507 A1 | 9/2007 |
| JP | 11-504530 A | 4/1999 |

(Continued)

*Primary Examiner* — Adam Baker
(74) *Attorney, Agent, or Firm* — Veros Legal Solutions, LLP (57) ABSTRACT

A low profile, lightweight hinged knee brace is provided for use in providing support to individuals having injuries to their ligaments. The brace includes an upper component that can be formed to fit the thigh of a wearer. The brace further includes a lower component that can likewise be formed to custom fit the calf of the wearer. Both the upper and lower components are encapsulated in a continuous liner. Between the upper and lower components are inflexible rigid members constructed of a lightweight yet durable material to provide strength and rigidity to the brace. The brace is constructed from a two dimensional structure which allows for malleability coupled to a formed three dimensional structure which provides stiffness and enhanced protection of the knee. Methods of treating injuries to a ligament of the knee are similarly provided.

7 Claims, 5 Drawing Sheets

(56) References Cited

U.S. PATENT DOCUMENTS

| | | | | |
|---|---|---|---|---|
| 5,336,161 A | * | 8/1994 | Lengyel | A61F 5/0125 602/16 |
| 5,554,104 A | * | 9/1996 | Grim | A61F 5/0125 602/16 |
| 5,608,599 A | | 3/1997 | Goldman | |
| 5,658,243 A | * | 8/1997 | Miller | A61F 5/0125 602/16 |
| 5,891,068 A | * | 4/1999 | Kenney | A61F 5/0111 602/16 |
| 5,947,913 A | | 9/1999 | Palumbo | |
| 6,027,466 A | | 2/2000 | Diefenbacher et al. | |
| 6,488,644 B1 | * | 12/2002 | Ostrom | A61F 5/0193 403/87 |
| 6,494,853 B1 | | 12/2002 | Rossi et al. | |
| 6,527,733 B1 | | 3/2003 | Ceriani et al. | |
| 7,410,471 B1 | | 8/2008 | Campbell et al. | |
| 8,657,772 B2 | | 2/2014 | Einarsson | |
| 2004/0054311 A1 | * | 3/2004 | Sterling | A61F 5/0123 602/26 |
| 2004/0068215 A1 | * | 4/2004 | Adelson | A61F 5/0123 602/26 |
| 2005/0209541 A1 | * | 9/2005 | Kenney | A61F 5/0125 602/16 |
| 2010/0121242 A1 | * | 5/2010 | Chiang | A61F 5/0123 602/26 |
| 2012/0016283 A1 | * | 1/2012 | Hollister | A61F 5/0123 602/14 |

FOREIGN PATENT DOCUMENTS

| | | |
|---|---|---|
| WO | 2005107659 A2 | 11/2005 |
| WO | 2013052358 A1 | 4/2013 |

* cited by examiner

LOW PROFILE KNEE BRACE AND METHOD OF USING SAME

CROSS-REFERENCE TO RELATED APPLICATIONS

This application claims priority to U.S. Provisional Application No. 62/039,716, filed on Aug. 20, 2014, the entire contents of which are hereby incorporated by reference.

BACKGROUND OF THE INVENTION

1. Field of the Invention

The present invention relates generally to a low profile orthopedic device and more specifically to a knee brace for supporting ligament instability.

2. Description of the Related Technology

Damaged ligaments, cartilage, and tendons in joints are not an uncommon occurrence, particularly with today's emphasis on physical activity and conditioning. Few injuries interfere with motion more than injuries to the knee. Knee injuries account for approximately 60% of all sports related injuries with nearly half of those injuries occurring to the ACL. ACL injury is most prevalent (1 in 1,750 persons) in patients between the ages of 15 and 45, due in no small measure to their more active lifestyle as well as higher participation in sports. A person who has torn their ACL has a 15 times greater risk of a second ACL injury during the initial 2 months after ACL reconstruction, and risk of ACL injury to the opposite knee is two times that of the restructured knee.

There are four main ligaments which hold the knee together: Anterior Cruciate Ligament (ACL), Posterior Cruciate Ligament (PCL), Medial Collateral Ligament (MCL) and Lateral Collateral Ligament (LCL). There are over 200,000 ACL injuries that occur in the United States annually. ACL injuries range from a partial ACL tear to a complete ACL tear to bone avulsions. Partial and complete ACL tears are repaired with sutures or reconstructed using a graft. Approximately 50% of ACL injuries occur with injuries to other structures of the knee. While less common than an ACL injury, injuries to the PCL account for between 3% to 20% of all knee ligament injuries. The collateral ligaments, MCL and LCL, are responsible for 25% of knee injuries in competitive athletes.

Treatments for ACL and other ligament injuries include surgical and non-surgical options. Braces are employed to promote support and stabilization while ligaments heal. In the case of ACL surgery, graft strength of a new ACL is considerably weaker than the native ACL during the first 12 months, so a brace during this early period helps protect it from harmful forces that occur in everyday life or in sports activity.

There exists numerous orthotic devices which are aimed to provide support and/or protect the knee joint, particularly in the context of ACL injury. Many knee braces have been designed to remediate injury by limiting unnatural knee joint movement to prevent further injury, protect the knee, and promote healing; however, most of the rigid knee braces are relatively heavy, have sub-optimal fit, and are bulky. More particularly, typical brace design includes a frame, padding, and strapping. The frame provides support, padding provides comfort, and strapping holds the brace on the leg. The frames, which are designed to provide structural support, can often be heavy, inflexible, and bulky. Removable padding is included to increase patient comfort and is removable so that it can be replaced if worn. Straps are also generally removable to allow for adjustability and to promote fit. Having removable straps and pads, however, adds bulk to the brace and bulk and discomfort can negatively impact patient compliance.

Orthotic bracing and support can promote healing and wellness through the benefit of natural motion. It would be a boon to individuals suffering from knee injury if suitable bracing and support devices were available to offer greater stability to a wearer while providing comfort and patient compliance. More particularly, there remains a need for orthopedic braces for treating moderate to severe ACL, PCL, MCL, and LCL instabilities. There is further a need for orthopedic braces which possess high strength without sacrificing wearability and comfort.

SUMMARY OF THE INVENTION

Disclosed is an orthotic brace for treating ACL, PCL, MCL, and/or LCL instabilities and osteoarthritis of the knee. The brace is constructed of lightweight material to increase comfort and wearer compliance. It possesses a very low profile and can fit under the clothing of the wearer. The brace comprises a customizable upper leg cuff that can be bent and molded to the shape of the wearer's leg region above the knee. The brace further includes a lower cuff region that is constructed from a thin, flexible material that can be bent and shaped to fit the posterior calf region of the wearer. The upper and lower cuffs are connected across rotatable hinges. Bilateral rigid members constructed of inflexible metal or metal alloy secure the upper and lower cuff components to the hinge assemblies.

A feature of the invention is a low profile knee brace for use in the treatment of ligament instability. Advantageously, the knee brace includes an upper thigh cuff component, a lower leg cuff component, and a liner encapsulating the upper thigh cuff component and the lower leg cuff component. The brace may further include bilateral hinge assemblies; wherein the upper thigh cuff component and the lower leg cuff component are pivotally attached to the hinge assemblies.

Also included in the brace is a plurality of straps for securing the brace to a wearer's leg. The straps are attached directly to the liner on at least one side of said brace to maintain a low profile. In certain aspects, the straps sit neither above nor below the brace but rather, sit in line with the brace. The straps may be attached by being sewn directly to the liner. In another aspect, the straps may be attached by ultrasonically welding the straps to the liner. In yet another aspect, the straps are riveted to the liner.

The brace further includes a rigid upper member and a rigid lower member secured to the hinge assemblies; wherein the rigid upper member and the rigid lower member further include a three dimensional structure having a recessed portion along a length of the rigid upper member and the rigid lower member. Preferably, the rigid members comprise lightweight titanium or titanium alloy.

The upper thigh cuff component may be constructed from a two dimensional metal or metal alloy component, which is embedded in the liner. Similarly, the lower leg cuff component may be constructed from a two dimensional metal or metal alloy component; wherein the metal or metal alloy component is embedded in the liner. Advantageously, the liner is non-removably attached to the metal or metal alloy components. Optionally, the liner may include a plurality of windows which may reveal the encapsulated metal/metal alloy component when the liner and metal/metal alloy component are integrally attached.

A method of treating ligament instability of the knee is also provided. The method can include providing a low profile knee brace for an individual in need thereof. The brace may advantageously include a malleable upper thigh cuff component, a malleable lower leg component, and a liner encapsulating the upper thigh cuff component and the lower leg cuff component. The brace may further include bilateral hinge assemblies for preventing hyperextension. Additionally, the brace may include a plurality of straps for securing the brace to a wearer's leg, wherein the plurality of straps are attached directly to the liner on at least one side of the brace. The brace may further include a pair of metal or metal alloy rigid members secured to the hinge assemblies. The use of said low profile knee brace provides support to said injured knee.

In one aspect, the liner is non-removably attached to the upper thigh cuff component and the lower leg component. The brace may be worn pre- or post-operatively. In another aspect, the brace is worn post-operatively following ligament repair surgery. The ligament can be a Anterior Cruciate Ligament (ACL), Posterior Cruciate Ligament (PCL), Medial Collateral Ligament (MCL), Lateral Collateral Ligament (LCL) or combinations thereof.

Also disclosed is a method of manufacturing a low profile brace for use in treating ACL injury. The method includes providing a first two dimensional metal/metal alloy component and a second two dimensional metal/metal alloy component and cutting said first and second metal/metal alloy components into an L shape. Advantageously, the metal/metal alloy component is a metal/metal alloy material. The method further includes providing a liner and permanently attaching the first and second metal/metal alloy components in the liner. The manufacturing method may also include the step of custom forming the first metal/metal alloy component and liner to the shape of a patient's upper thigh as well as custom forming the second metal/metal alloy component and liner to the shape of a patient's lower calf. A medial hinge assembly may be provided and the first metal/metal alloy component and liner may be engagingly connected to the upper portion of the medial hinge assembly and the second metal/metal alloy component and liner may be engagingly connected to the lower portion of a medial hinge assembly. The manufacturing method may further include providing a first and second three dimensional lateral rigid members; wherein the rigid members are constructed of metal/metal alloy. The metal/metal alloy may be titanium or titanium alloy.

The first lateral rigid member may be secured to the first metal/metal alloy component and liner; and the second lateral rigid member may be secured to the second metal/metal alloy component and liner. Also provided is a lateral hinge assembly, wherein engagingly connecting first lateral rigid member is engagingly connected to an upper portion of the lateral hinge assembly; and the second lateral rigid member is engagingly connected to a lower portion of the lateral hinge assembly. Optionally, the liner further includes an antimicrobial coating. The liner may be waterproof. In certain aspects, the liner can include a plurality of windows to expose at least one of the first or second metal/metal alloy components.

Advantageously, the manufacturing method includes attaching a plurality of straps directly to the liner. This direct attachment can be accomplished by sewing the straps directly to the liner.

The first and second titanium alloy components are capable of flex with force, whereas the first and second three dimensional lateral rigid members are substantially inflexible.

DETAILED DESCRIPTION OF CERTAIN INVENTIVE EMBODIMENTS

Embodiments of this application relate to orthopedic braces for use in treating a variety of injuries to the knee and surrounding ligaments. More particularly, embodiments of the brace disclosed herein are intended for use in activities of daily living for patients with ACL deficiencies, collateral ligament deficiencies, hyperextension injury, or for prophylactic use. As will be described in greater detail below, the brace is designed to address weight, strength, support, and aesthetic requirements for pre- and post-operative individuals having ligament damage particularly individuals who are engaged in an active lifestyle.

The brace as described and claimed herein addresses the shortcomings of prior art devices by greatly enhancing patient comfort and therefore patient compliance. Compliance is driven primarily by comfort; if a brace is not comfortable, a patient will not wear it. Comfort is in turn driven by the profile, weight, and fit of a brace. Embodiments of the brace disclosed herein include a low profile knee brace that is both lightweight and provides structural strength to a patient's knee.

Figure 3:
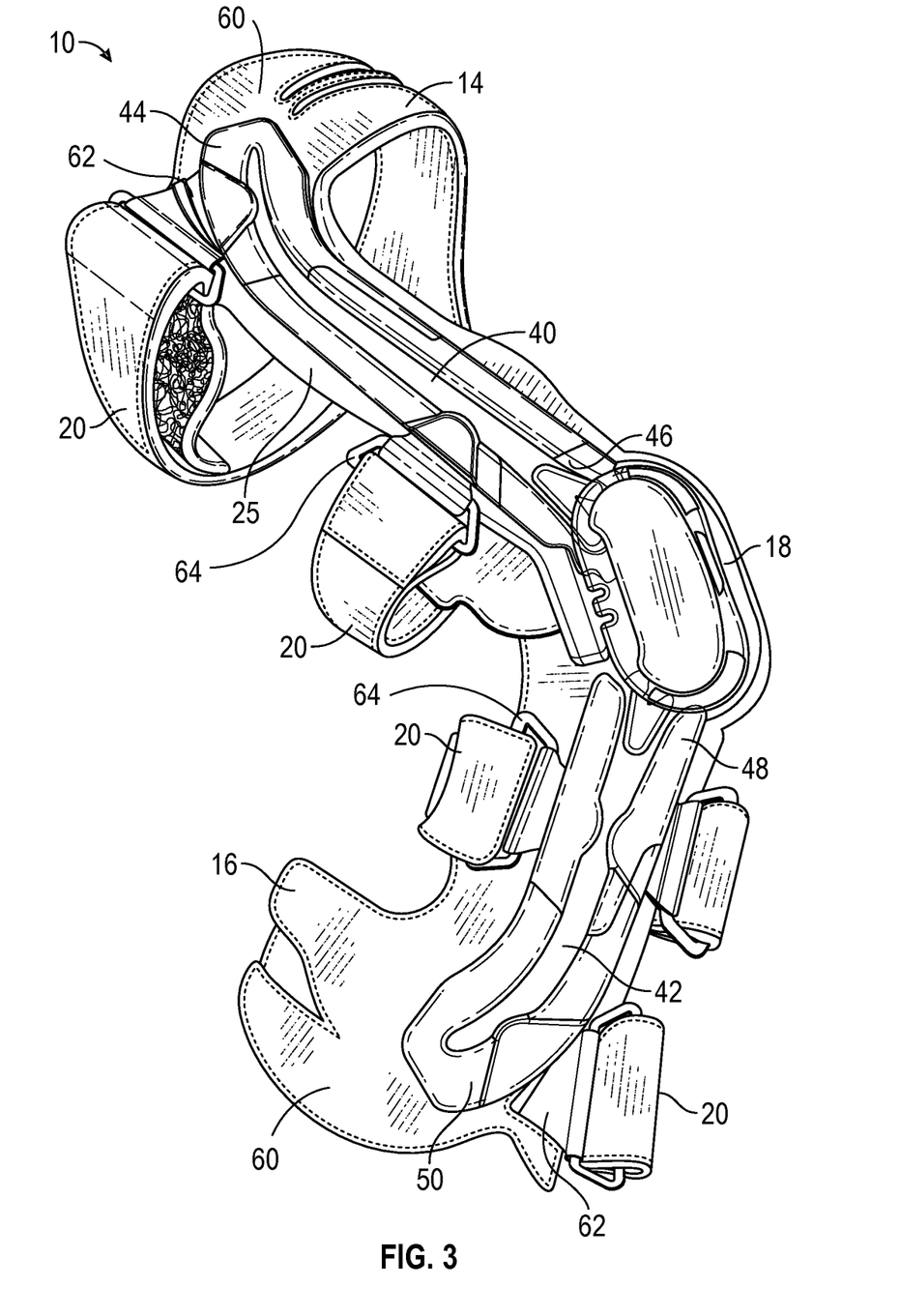
FIG. 3 is a lateral side view of the brace of FIG. 1.
Figure 4:
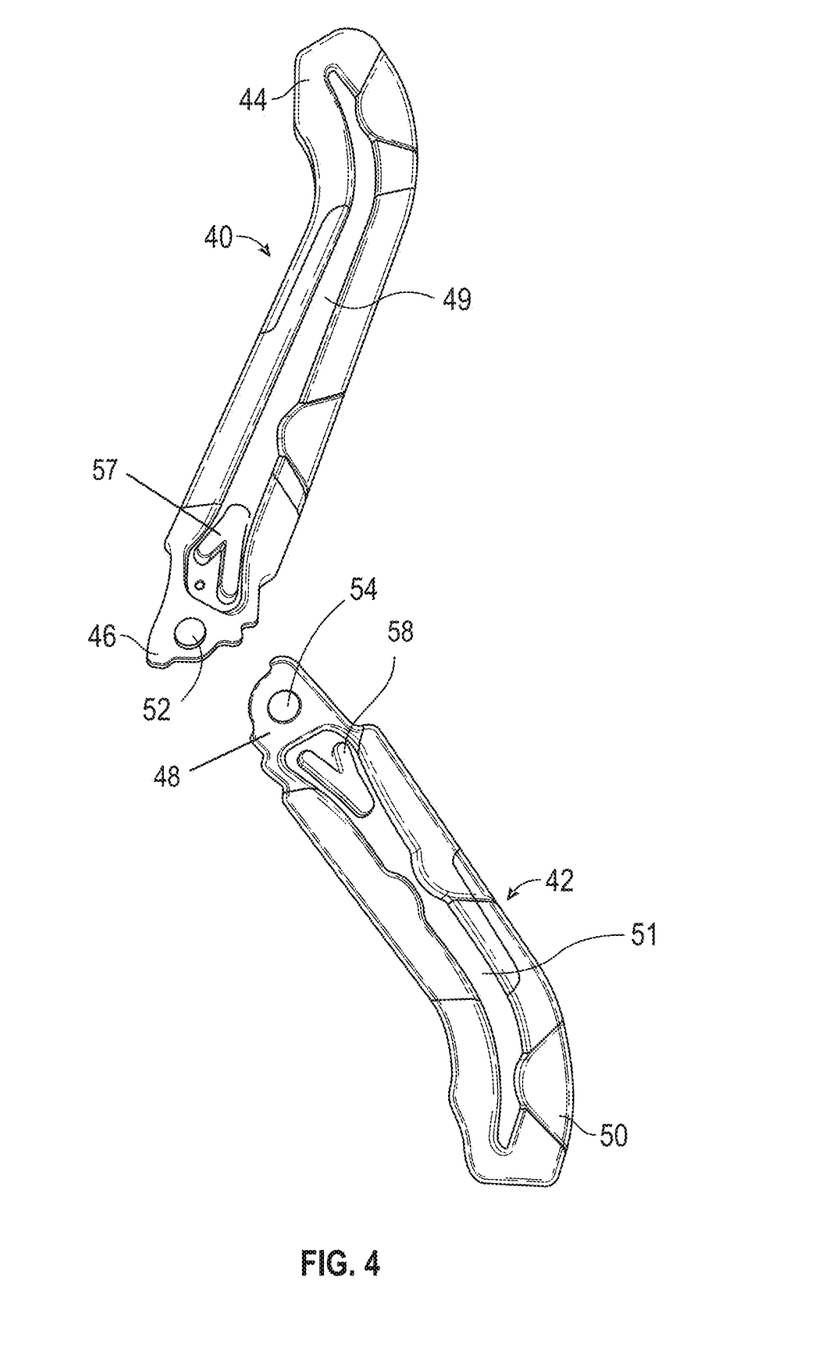
FIG. 4 are perspective views of the upper and lower rigid members of a brace.

Thus, embodiments of the invention relate to a brace having a very low profile while maintaining stability and support for the user. With an enhanced comfort and reduced bulkiness, the disclosed brace promotes greater user compliance. Features of the brace include, without limitation, a lightweight construction that is less bulky than prior art devices. Bulkiness is reduced not only by the use of a lightweight metal or metal alloy such as titanium or titanium alloy in the construction of the brace but also in the integration of a liner which is continuous and encapsulates portions of the relatively thin frame. The liner provides enhanced comfort, reduced profile, and additional structural support to the brace. The primary goal of the brace disclosed herein is to improve patient compliance. It is a goal of the invention to lower the base profile while still providing a suitable brace for ACL therapy as an ACL brace must have a certain degree of strength to provide stability and support. The metal/metal alloy is selected to provide this strength and at the same time address the issue of brace weight. Moreover, as will be described in greater detail below, the brace disclosed herein combines stiffness and malleability in a manner which promotes motion and activities of daily living for a patient. A brace that is too stiff may hinder fit because it does not flex with the wearer's muscles and a brace that is too malleable will not provide adequate support. By striking the balance between malleability and stiffness, the disclosed brace promotes patient comfort and compliance while affording the necessary structural support. The rigid lateral bars as will be described with reference to FIGS. 3 and 4 are a three dimensional configuration such that they are very rigid. These lateral rigid members give the brace significant strength due to a large moment of inertia as compared to a two dimensional configuration. The cuff and medial side of the brace are a flat two dimensional configuration and afford an acceptable level of malleability to provide a small amount of movement as a patient's muscles flex.

A better understanding of the various features of the invention can be gleaned from the following description read in conjunction with the accompanying drawings in which like reference characters refer to like elements. While the disclosure may be susceptible to various modifications and alternative constructions, certain illustrative features are shown in the drawings and are described in detail below. It will be understood, however, that there is no intention to limit the disclosure to the specific embodiments disclosed, but to the contrary, the intention is to cover all modifications, alternative constructions, combinations, and equivalents falling within the spirit and scope of the disclosure.

Furthermore, it will be appreciated that unless a term is expressly defined in this patent to possess a described meaning, there is no intent to limit the meaning of such term, either expressly or indirectly, beyond its plain or ordinary meaning.

For ease of understanding the disclosed features of an orthopedic device, the anterior and posterior portions of the orthopedic device are described independently. However, the anterior and posterior portions of the orthopedic device function together to support and stabilize anatomical portions of the wearer of the device. As used herein, "proximal" has its ordinary meaning and refers to a location situated next to or near the point of attachment or origin or a central point, or located toward the center of the body. Likewise, the term "distal" has its ordinary meaning and refers to a location that is situated away from the point of attachment or origin or central point, or located away from the center of the body. The term "medial" refers to a position that is closer to the midline of the body, whereas the term "lateral" refers to a position further from the midline of the body. The terms "upper" and "lower" describe the position of certain elements as being either above or below the hinge portions of the brace assembly. An "upper" element is above the hinge and knee joint, whereas a "lower" element is below the hinges and knee joint. The term "posterior" also has its ordinary meaning and refers to a location that is behind or to the rear of another location. Lastly, the term "anterior" has its ordinary meaning and refers to a location that is ahead of or to the front of another location.

The terms "rigid," "flexible," "malleable" and "resilient" may be used herein to distinguish portions of certain features of the orthopedic device. The term "rigid" is intended to mean an element of the device is generally or substantially inflexible. Within the context of frame or support members or shells that are "rigid," it is intended to indicate that they do not lose their overall shape when force is applied. The term "flexible" or "malleable", by contrast, is intended to encompass features that are capable of bending or flex under load.

Figure 1:
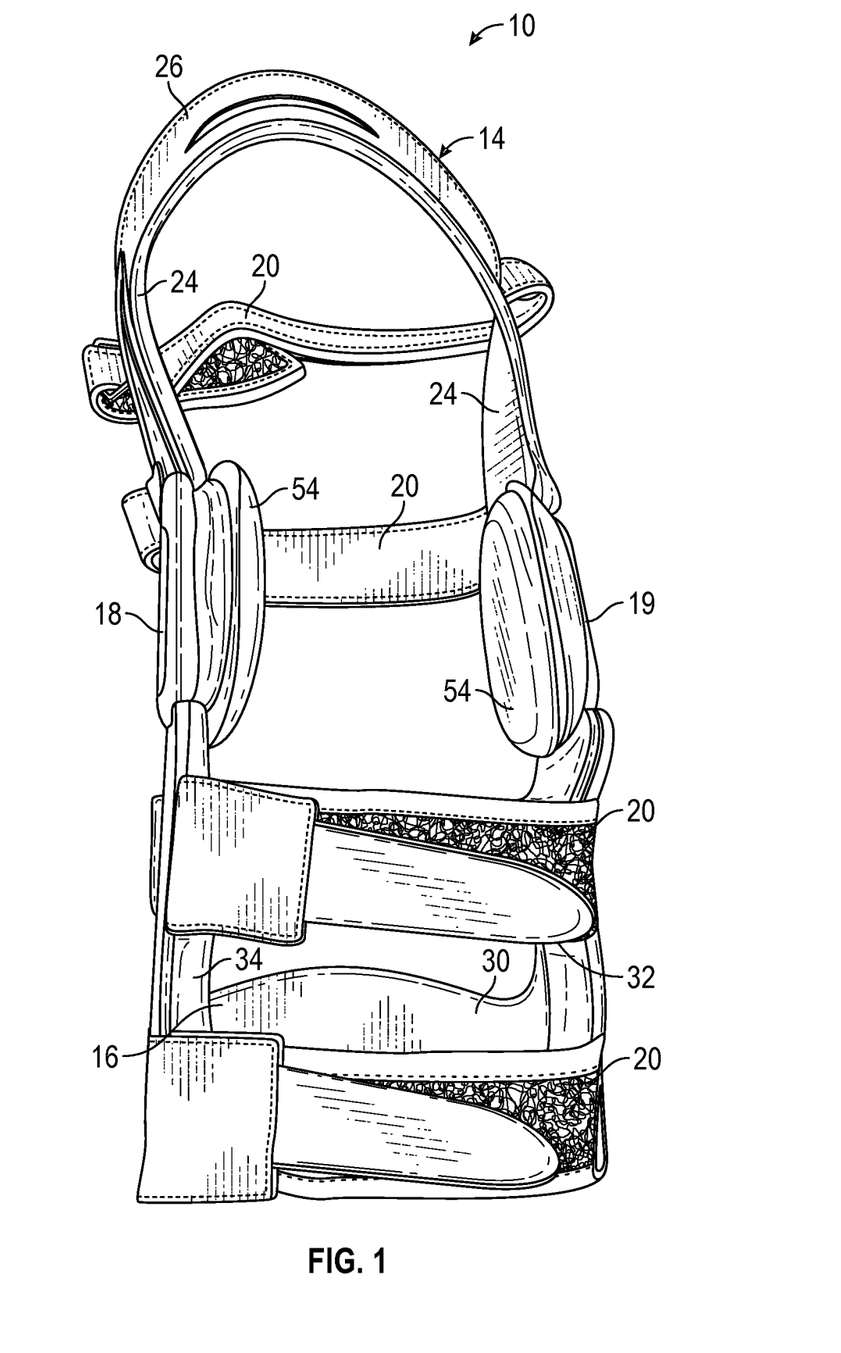
FIG. 1 is a perspective anterior view of an orthotic brace for use in treating ligament instabilities.

Referring initially to FIG. 1, disclosed herein is an orthopedic brace assembly 10. For the purposes of illustration, the brace 10 is configured for securing to a right leg of a wearer. However, it is readily apparent to the skilled artisan from the teaching provided herein that the brace assembly 10 can be adapted for securing to the opposite leg of the wearer. One of the advantages of the brace disclosed herein is its extremely light weight and low profile construction. The brace 10 provides durable support for treatment of ACL, PCL, MCL, and LCL instabilities while still offering a low profile such that the brace 10 can be worn under clothing. As illustrated, the brace 10 is constructed for use in the treatment of ligament instabilities of the knee. However, it will also be appreciated that, with slight modification to include features to reduce load, and without deviating from the spirit of the invention, the brace can also be used to alleviate symptoms of osteoarthritis (OA). Also, because of its lightweight design, the brace 10 will enable greater patient compliance with wear time. More particularly, the featherweight materials and custom fit enhance comfort and thereby user compliance with increased wear time more likely.

The brace assembly 10 is shown to generally include an upper cuff component or thigh cuff component 14, a lower cuff component or calf cuff component 16, and a pair of hinge assemblies 18, 19. The brace 10 is preferably used to stabilize the knee and also can be used to support the knee joint during rehabilitation after an injury. A feature of the brace 10 is its low profile construction. The upper cuff 14 and lower cuff component 16 are conformable to the thigh and lower calf of the wearer, respectively. The thigh cuff component 14 and the lower cuff component 16 are formed from a thin, metal or metal alloy material which provides structural support while still allowing for slight flex upon exertion of force. As used herein, the metal or metal alloy may include any number of metals which are both relatively light weight while still providing structural strength to the brace. Suitable metal or metal alloys can include, without limitation, aluminum, steel, magnesium, titanium, or combinations thereof. Alternatively, the metal can be a molded carbon fiber composite. In preferred embodiments, the metal is a titanium or titanium alloy. The thigh cuff component 14 is configured to fit the anterior portion of the wearer's leg above the knee and the lower cuff component 16 is configured to fit the calf of the wearer. In a preferred embodiment, the thigh cuff component 14 and lower cuff component 16 are custom fit to the wearer's leg. The brace frame, comprised of the upper cuff 14 and lower cuff 16, are encapsulated by a single continuous liner as will be described in greater detail below.

The thigh cuff component 14 includes two downwardly extending portions 24 and 25 positioned medially and laterally relative to the wearer's knee, respectively. A femoral transverse portion 26 of the thigh component 14 is custom formed to conform to the wearer's thigh to provide structure and strength as well as a customized fit. Advantageously, the thigh cuff component 14 anchors the femur and provides a custom fit to the top of the anterior thigh.

The lower cuff component 16 includes a posterior cuff 30, having a medial arm 32 and a lateral arm 34 extending therefrom. The lower cuff component 16 has substantially the same structure as the upper thigh cuff component 14, but is sized to conform to the lower leg of the user. The lower cuff 30 has substantially the same configuration as the upper thigh cuff component 14, but the arcuate shape thereof is sized comparatively smaller to snugly conformingly engage the calf of the lower leg.

The brace 10 maintains the thigh and calf in proper alignment and promotes stabilization. The hinges 18, 19 are configured with a limited range of rotation to prevent hyperextension of the lower leg.

Medial hinge 19 also can include a hinge deflector for preventing interference between medial hinges when a user is wearing a knee brace on each leg such as the deflector described in U.S. Pat. No. 6,890,314. The hinge deflector acts as a shield to the internal components of the medial hinge 19 and deflects the opposite medial hinge, preventing the hinges from locking together. The hinges 18, 19 can be any of a number of suitable hinge assemblies including, for example, the FourcePoint™ hinge (DJO Global, Vista, Calif.). Advantageously, the hinge assemblies are configured to react during leg extension and offer an increasing resistance in the last 35 degrees of extension, in order to reduce extension shock and increase posterior tibial loads. A resilient pad 56 can be provided to cushion the knee joint from the rigid hinges 18, 19. In addition to use in injuries or instabilities of ligaments, it will be appreciated by a skilled artisan, the hinge and pads can be modified for other treatment modalities such as osteoarthritis.

As will be described more particularly with reference to FIG. 5, the brace 10 is also provided with a plurality of adjustable straps 20 for engaging the brace at two points on opposite sides of the hinge to stabilize the weakened joint throughout it range of motion. The plurality of straps further act to secure the upper cuff 14 and lower cuff component 16 to the respective thigh and calf portions of the leg. As illustrated, the straps 20 include VELCRO® loop and hook material which can attach the straps and secure the brace in place.

Figures 2A, 2B:
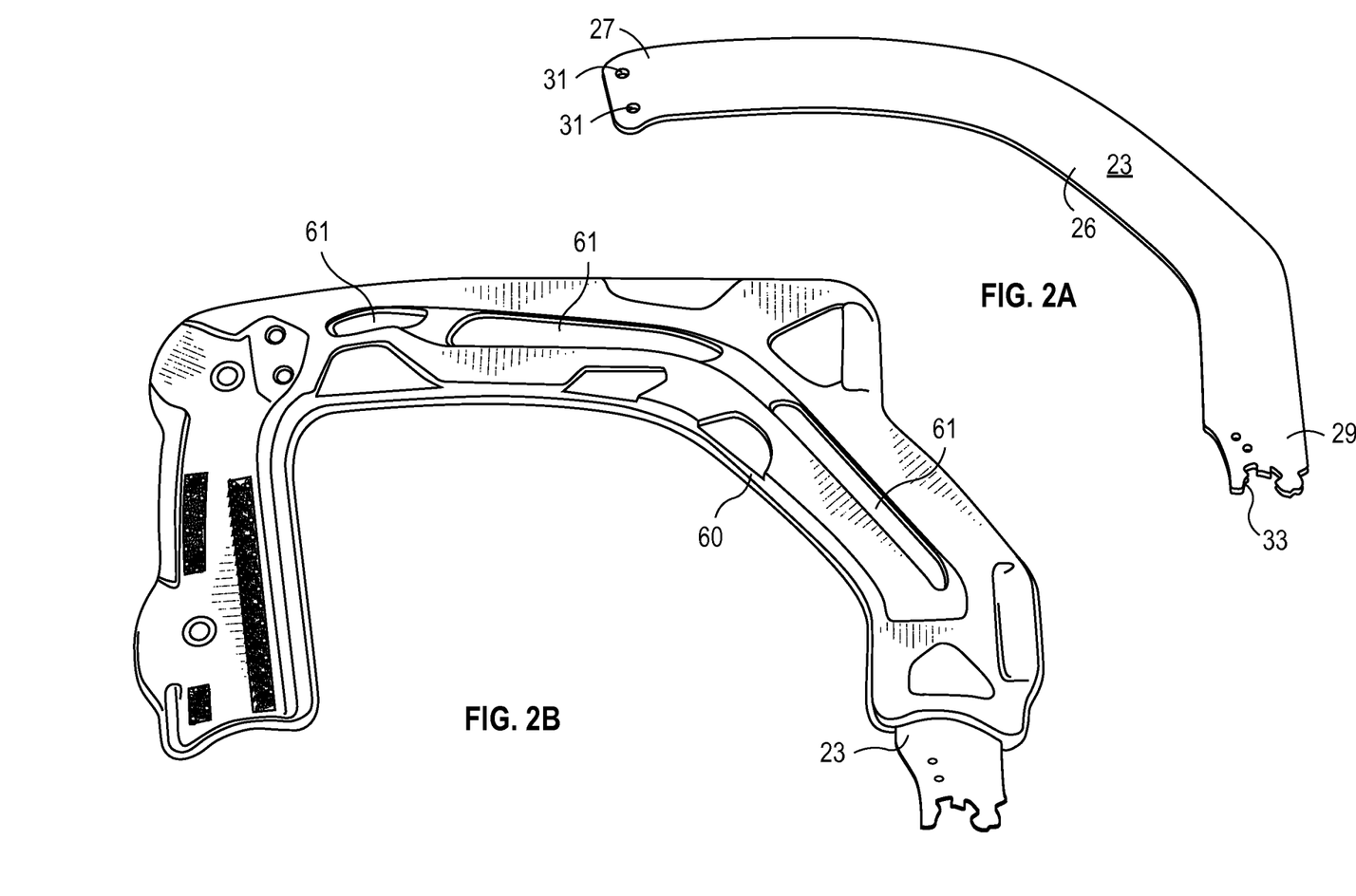
FIG. 2A illustrates the metal/metal alloy component of the upper thigh cuff feature.
FIG. 2B is a perspective view of the metal/metal alloy component of FIG. 2A encapsulated in a liner.

A feature of the present invention is a two dimensional configuration of the upper cuff component 14 and lower cuff component 16 coupled with lateral rigid members. In some aspects, the lateral rigid members are three dimensionally constructed lateral rigid members. Two dimensional construction of thin metal/metal alloy allows for lightweight structural support for the knee with a degree of malleability for the portions of the brace which are positioned around the patient's thigh and calf region. As used herein, two dimensional construction refers to a process by which flat metal/metal alloy is cut into a substantially L-shape and the flat metal/metal alloy is then integrally encapsulated with a liner (as will be described in greater detail below). The flat upper cuff component and flat lower cuff component can then be formed to provide a custom fit and to conform to the shape of a patient's thigh and calf anatomy. The two dimensional fabrication of the upper cuff component 14 is illustrated FIGS. 2A and 2B. FIG. 2A illustrates a metal/metal alloy component 23 of the upper cuff component 14 having a first end 27 and a second end 29. Between the first and second ends 27, 29 there is the femoral transverse portion 26. At the first end 27, there is a plurality of apertures 31 configured for attachment to the lateral rigid member (not shown). At the second end 29, there is a gear joint 33 for receiving a gear.

FIG. 2B illustrates the metal/metal alloy component of FIG. 2A encapsulated in a liner 60. As illustrated, the liner 60 is shown as encapsulating the metal/metal alloy component 23 of upper thigh cuff component 14 but it will be appreciated that both the upper thigh cuff and lower cuff are disposed within a liner and the liner is integrally attached to said upper and said lower cuffs. The liner 60 blends the more malleable portions of the brace with relatively inflexible portions of the brace and provides added structural support to the brace. The liner is advantageously continuous with the brace and integrally formed about the brace to achieve a low profile as compared to braces having removable liners to provide padding and comfort. Additionally, the integral encapsulation of the metal or metal alloy element by the liner provides further structural support to the brace. The liner 60 is comprised of a plurality of layers. The outside portion of the liner 60 is comprised of a fabric having an antimicrobial coating and an EVA foam. These layers are thermoformed and an adhesive is applied inside the thermoformed portion and the metal/metal alloy frame is inserted. A further layer of foam may be added. Advantageously, the interior layer (i.e., the layer closest to a patient's skin) may also include a fabric layer having texturing to promote comfort such as suede or other suitable finish with an antimicrobial coating. In some embodiments, the liner is waterproof. As illustrated in FIG. 2B, the liner 60 can include a plurality of windows 61. The plurality of windows 61 are cut out of the liner 60 and reveal the metal/metal alloy component integrally encapsulated within the liner. In a preferred embodiment, the metal/metal alloy is titanium.

Turning to FIG. 3, FIG. 3 is a lateral side view of a brace as described herein. The brace 10 includes a thigh cuff component 14 encapsulated by a liner 60. Similarly, the brace includes a lower cuff component 16 that is likewise encapsulated by a liner 60. The upper thigh cuff 14 and lower cuff component 16 includes a plurality of strap elements 20 configured to secure the brace to the wearer's leg. The plurality of strap elements 20 can be threaded through a ring 64 which is attached to a plurality of strap tabs 62. The strap taps 62 are attached on the lateral side of the brace to the rigid upper and lower members 40, 42 respectively (described below).

Still with reference to FIG. 3, the two dimensional metal/metal alloy components of the upper and lower cuff components and liner described above afford a degree of malleability to the brace. As illustrated in FIG. 3, on the lateral side of the brace 10, there is a lateral rigid upper member 40 and a lateral rigid lower member 42. These lateral rigid members provide enhanced protection by providing rigid, stiff support to the lateral side of the brace. Attached to the lateral downwardly extending portion 25 of the thigh cuff 14 is a substantially rigid upper member 40 having a proximal end 44 and a distal end 46 attaches to the lateral downwardly extending portion 25 of the thigh cuff 14 at the proximal end 44 of the rigid member 40. The rigid upper member 40 is constructed from a lightweight but inflexible material that provides strength and support to the brace 10. Advantageously, the material is titanium. The proximal end 44 of the rigid upper member 40 is secured to the lateral downwardly extending portion 25 of the thigh cuff 14 and the distal end 46 of the rigid upper member is pivotally attached to hinge assemblies 18, 19 (both are shown in FIG. 1, whereas FIG. 3, which is a lateral side view, shows only hinge assembly 18). The corresponding lower rigid member 42 of the lower cuff component 16 has a proximal end 48 and a distal end 50 and is pivotally attached to the hinge assemblies 18, 19 at the proximal end 48 of the lower rigid member 42.

FIG. 4 is a perspective view of the upper rigid member 40 and lower rigid member 42 separated from the brace 10. The upper and lower rigid members 40, 42 are three dimensional in construction and include recessed channels 49, 51 respectively. This three dimensional construction give the brace significant strength due to a large moment of inertia as compared to a two dimensional configuration. A substantially y-shaped portion 57 of recessed channel 49 is disposed at distal end 46 of the rigid upper member, substantially y-shaped portion 57 being further raised outwardly away from the wearer's leg from adjacent portions of recessed channel 49 that separate substantially y-shaped portion 57 from the respective perimeter of upper rigid member 40. At the distal end 46 of the upper rigid member 40, there is an aperture 52 configured to receive a gear (not shown). The gear can be stainless steel and can be press fit into the aperture 52 for engagement with a hinge assembly. Similarly, a substantially y-shaped portion 58 of recessed channel 51 is disposed at proximal end 48 of rigid lower member 42, substantially y-shaped portion 58 being further raised outwardly away from the wearer's leg from adjacent portions of recessed channel 51 that separate substantially y-shaped portion 58 from the respective perimeter of lower rigid member 42. At the proximal end 48 of the rigid lower member 42, there is an aperture 54. A gear (not shown) can be press fit into the aperture 54 for engagement with the hinge assembly. The lateral upper and lower rigid members are configured to be attached to be permanently secured to the upper and lower cuff components. In one aspect, the rigid upper and lower components are attached to the upper and lower cuff components by integrated attachment points and rivets.

Figure 5:
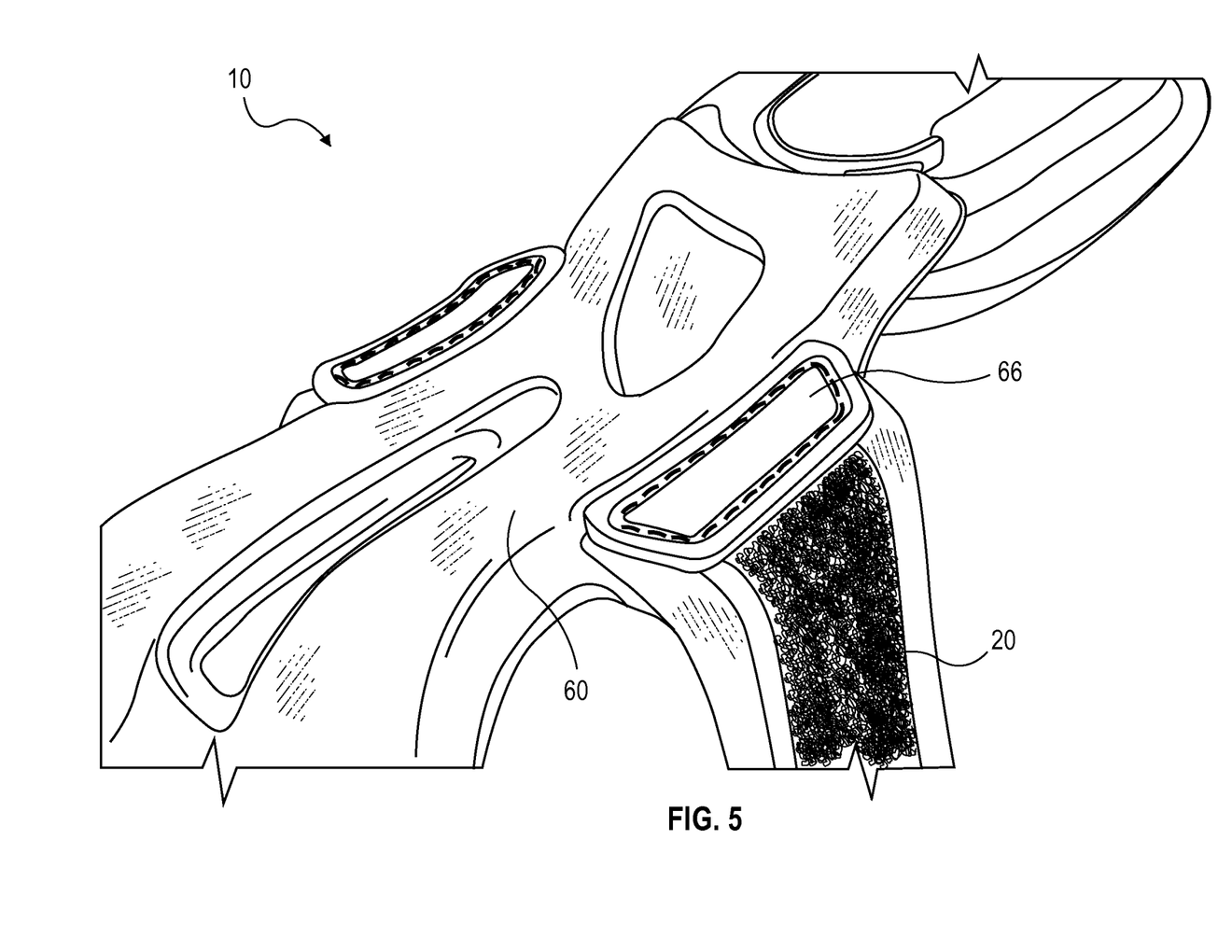
FIG. 5 is an enlarged medial side view of a brace having strap elements attached directly to a liner.

Turning now to FIG. 5, FIG. 5 is an enlarged view of the medial side of a brace 10 to illustrate the attachment of the straps of the brace directly to the liner 60. Typically, prior art braces include straps with tabs that are connected directly to the metal frame of a brace. However, the presently disclosed brace includes straps attached directly to at least one side of the liner rather than to the metal frame of the brace. As illustrated in FIG. 5, at the medial side of the brace, there is a plurality strap elements 20 which include a plurality of medial sew tabs 66. The medial sew tabs 66 are sewn or otherwise non-removably attached directly to the liner 60. Also included in the brace is a plurality of straps for securing the brace to a wearer's leg. As is illustrated in FIG. 5, the sew tabs 66 do not protrude above or below the structural component of the brace. Thus, in certain aspects, the straps sit neither above nor below the brace but rather, sit in line with the brace. The straps may be attached by being sewn directly to the liner. In another aspect, the straps may be attached by ultrasonically welding the straps to the liner. In yet another aspect, the straps are riveted to the liner. The plurality of medial sew tabs 66 sit in line with the brace frame to reduce bulk associated with the removable straps of prior art braces because it is integrally attached to the liner 60. As illustrated in FIG. 5, the sew tabs 66 are permanently affixed or attached to the liner. It will, however, be appreciated that it would be possible to achieve the described low profile by removably attaching the sew tabs 66 to the liner 60. For example, the liner can include one of a VELCRO® loop and hook material sewn directly to the liner and the opposite VELCRO® loop and hook material could be attached to a strap such that the strap, when attached to the line, sat in line with the brace, but could be removed if required.

Methods of treating ligament instability of the knee are likewise provided. The ligament instabilities can include injury to a patient's ACL, PCL, MCL, LCL, or combinations thereof. The method includes identifying an individual presenting with a ligament instability and providing the individual with a low profile knee brace having a malleable upper thigh cuff component; a malleable lower leg component; a liner encapsulating the upper thigh cuff component and the lower leg cuff component; bilateral hinge assemblies; a plurality of straps for securing the brace to a wearer's leg, wherein the plurality of straps are attached directly to said liner on at least one side of the brace; and a pair of metal/metal alloy rigid members secured to the hinge assemblies. In one aspect, the metal/metal alloy is a titanium or titanium alloy. The metal/metal alloy rigid members comprise a three dimensional configuration, each having a length with a recess defining the length of each rigid member. The three dimensional rigid members, constructed of metal/metal alloy, are very rigid while still maintaining a lightweight profile. The use of the low profile knee brace described herein provides support to the injured knee. The upper and lower cuff components are encapsulated by a liner, which provides additional structural support to the malleable elements while still affording comfort without bulkiness.

In one aspect, the method of treating ligament instability of the knee can be employed prior to surgical intervention for correcting damage to a knee ligament. In other aspects, the method can be employed as part of a patient's postoperative rehabilitation after a ligament reconstruction. Use of a brace as described herein can protect a patient's knee from further injury while enabling the patient to return to activities of daily living as well as pursue athletic endeavors. In yet another aspect, a method of preventing knee injuries is contemplated. Given the physicality of a number of sports activities, a brace as described herein can be used to prevent knee injuries. Exemplary sports activities include, without limitation, skiing, football, snowboarding, soccer, basketball, volleyball, professional rodeo, rugby, lacrosse, water sports or similar. The brace is similarly well suited for use by individuals who are engaged in activities of daily living and who have ACL deficiencies, collateral ligament deficiencies, hyperextension injury, or who wear a brace for prophylactic use. The lightweight construction, combination of rigid and malleable portions, reduced profile, and liner integral to the malleable portions of the brace provide a very lightweight, comfortable, yet strong and functional brace. As comfort drives compliance, the use of the brace described herein promotes patient compliance.

Another feature of the invention is the optional inclusion of an integrated biofeedback sensor in electronic communication with the orthotic brace. In one aspect, the biofeedback sensor is attached to the underside of the upper and/or lower rigid members. The biofeedback sensor may comprise a low energy wireless technology such as Bluetooth 4.0 with a sensor application for IOS and Android operating systems. The sensor is configured to measure wear time to monitor wearer compliance with the brace. An additional feature of the biofeedback sensor is a temperature sensor, either direct or IR (off surface sensing). The sensor can likewise optionally include a 3 axis accelerometer, a 3 axis gyroscope, a magnetometer, a humidity meter, a proximity sensor, a barometric pressure monitor, and/or monitors for peripheral capillary oxygen saturation, an indoor location system such as iBeacon® for GPS monitoring, a monitor for counting cycles of angular flexes, or combinations thereof. Other features can include an audible and/or tactile feedback sensor to alert the patient if and when certain parameters are achieved, exceeded, or not yet achieved.

The biofeedback sensor is preferably powered by an alkaline power source or lithium polymer rechargeable battery. The biofeedback sensor is removably attached to the orthotic brace via a micro USB or inductive charging. In the case of inductive charging, the device is hermetically sealed to allow for a waterproof or substantially water resistant structure.

The biofeedback sensor provides data analytics and reporting capabilities. In communication with a smartphone device, data can be uploaded from the sensor to the smartphone. The smartphone device is configured to organize the data to produce a report relating to usage, wear time, or other parameters measured by the biosensor. The report provides meaningful information to the patient and/or health care provider and treatment modalities can be modified based upon the data generated and reported.

Although the present invention has been described in terms of certain preferred features, other features of the invention including variations in dimensions, configuration and materials will be apparent to those of skill in the art in view of the disclosure herein. In addition, all features detailed in connection with any one aspect herein can be readily adapted for use in other aspects herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A low profile knee brace for use in the treatment of injury to a ligament, comprising:
    an upper thigh cuff component;
    a lower leg cuff component;
    a continuous non-removable liner encapsulating the upper thigh cuff component and the lower leg cuff component;
    bilateral hinge assemblies, wherein the upper thigh cuff component and the lower leg cuff component are pivotally attached to the hinge assemblies;
    a plurality of straps for securing the brace to a wearer's leg, wherein each of the plurality of straps is attached directly to a respective portion of the liner;
    a rigid upper member having a distal end pivotally coupled, at a fixed position on the distal end, to a separate fixed position on an upper portion of one of the hinge assemblies; and
    a rigid lower member having a proximal end pivotally coupled, at a fixed position on the proximal end, to a separate fixed position on a lower portion of the one of the hinge assemblies, each of the rigid upper member and the rigid lower member having a three dimensional structure comprising:
        a recessed channel extending centrally along substantially an entire respective length of extension of the rigid upper member or of the rigid lower member, wherein the recessed channel comprises substantially continuous portions of the rigid upper member or of the rigid lower member, the recessed channel is not an aperture, and the recessed channel is recessed inward toward the wearer's leg with respect to substantially an entire respective perimeter of the rigid upper member or of the rigid lower member, the recessed channel further comprising a substantially y-shaped portion disposed at the proximal end of the rigid lower member or at the distal end of the rigid upper member, the substantially y-shaped portion further raised outwardly away from the wearer's leg from adjacent portions of the recessed channel that separate the substantially y-shaped portion from the respective perimeter of the rigid upper member or of the rigid lower member;
        the respective perimeter of the rigid upper member or of the rigid lower member further comprising at least one portion further raised from adjacent portions of the respective perimeter and having a strap tab attached thereunder, the strap tab attached to a ring configured to receive a portion of a respective one of the plurality of straps such that the respective one of the plurality of straps sits in line with the respective rigid upper member or rigid lower member;
    wherein the rigid members comprise a metal or metal alloy selected from the group consisting of titanium, aluminum, steel, magnesium, and combinations thereof.

2. The brace of claim 1, wherein:
    the upper thigh cuff component is constructed from a two dimensional titanium alloy component; and
    the titanium alloy component is embedded in the liner.

3. The brace of claim 1, wherein the lower leg cuff component is constructed from a two dimensional titanium component embedded in the liner.

4. The brace of claim 1, wherein the upper thigh cuff component and the lower leg cuff component are each constructed from two dimensional titanium embedded in the liner.

5. The brace of claim 1, wherein the liner comprises a combination of foam and fabric padding.

6. The brace of claim 1, wherein the liner further comprises a plurality of windows.

7. A low profile knee brace, comprising:
    a malleable leg cuff assembly, comprising:
        an upper thigh cuff component capable of being formed to custom fit the thigh of a wearer;
        a lower leg cuff component capable of being formed to custom fit the calf of a wearer; and
        a continuous non-removable liner encapsulating the leg cuff assembly;
    a hinge assembly;
    a lateral upper rigid member connected to the upper thigh cuff component, a distal end of the lateral upper rigid member being pivotally coupled, at a fixed position on the distal end, to a separate fixed position on an upper portion of the hinge assembly;
    a lateral lower rigid member connected to the lower leg cuff component, a proximal end of the lateral lower rigid member being pivotally coupled, at a fixed position on the proximal end, to a separate fixed position on a lower portion of the hinge assembly;
    wherein each of the lateral upper member and the lateral lower member has a three dimensional structure comprising:
        a recessed channel extending centrally along substantially an entire respective length of extension of the lateral upper member or of the lateral lower member, wherein the recessed channel comprises substantially continuous portions of the lateral upper rigid member or of the lateral lower rigid member, the recessed channel is not an aperture, and the recessed channel is recessed Inward toward the wearer's leg with respect to substantially an entire respective perimeter of the lateral upper member or of the lateral lower member, the recessed channel further comprising a substantially y-shaped portion disposed at the proximal end of the rigid lower member or at the distal end of the rigid upper member, the substantially y-shaped portion further raised outwardly away from the wearer's leg from adjacent portions of the recessed channel that separate the substantially y-shaped portion from the respective perimeter of the rigid upper member or of the rigid lower member; and
        the respective perimeter of the rigid upper member or of the rigid lower member further comprising at least one portion further raised from adjacent portions of the respective perimeter and having a strap tab attached thereunder, the strap tab attached to a ring configured to receive a portion of a respective strap such that the respective strap sits in line with the respective rigid upper member or the rigid lower member;

wherein the rigid members comprise a metal or metal alloy selected from the group consisting of titanium, aluminum, steel, magnesium, and combinations thereof;

and the respective straps.

\* \* \* \* \*